(12) United States Patent
Pineau et al.

(10) Patent No.: US 6,296,856 B1
(45) Date of Patent: *Oct. 2, 2001

(54) POLYHOLOSIDE COMPOSITIONS FOR BENEFICIALLY TREATING THE SKIN

(75) Inventors: Nathalie Pineau, Poitiers; Lionel Breton, Versailles, both of (FR)

(73) Assignee: Societe l'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/891,194

(22) Filed: Jul. 10, 1997

(30) Foreign Application Priority Data

Jul. 10, 1996 (FR) .................................................. 96 08616

(51) Int. Cl.[7] .............................. A61K 7/00; A61K 6/00; A61K 7/021
(52) U.S. Cl. ........................... 424/401; 424/63; 514/844; 514/842
(58) Field of Search ..................... 424/401, 63; 514/844, 514/847

(56) References Cited

U.S. PATENT DOCUMENTS 5,409,703 * 4/1995 McAnalley ............................ 424/435
5,629,015 * 5/1997 Ribier et al. .......................... 424/450

FOREIGN PATENT DOCUMENTS 4221753 7/1994 (DE) .............................. C08B/37/00

OTHER PUBLICATIONS

Drug Research, vol. 35, No. 7, 1985, pp. 1069–1075, XP000646167, Wagner et al.

* cited by examiner

Primary Examiner—John Kight
Assistant Examiner—D. Faulkner
(74) Attorney, Agent, or Firm—Burns, Doane, Swecker & Mathis, L.L.P.

(57) ABSTRACT

Cosmetic/pharmaceutical/dermatological compositions suited for promoting desquamation of the skin of a mammalian organism in need of such treatment and/or to stimulate epidermal renewal and thus to combat intrinsic and/or extrinsic aging thereof, via topically applying same to the skin of such organism, comprise a cutaneous aging-combating effective amount of at least one polyholoside, preferably a heterogeneous polyholoside, in a topically applicable, cosmetically/pharmaceutically/dermatologically acceptable vehicle, carrier or diluent therefor.

19 Claims, No Drawings

POLYHOLOSIDE COMPOSITIONS FOR BENEFICIALLY TREATING THE SKIN

CROSS-REFERENCE TO COMPANION APPLICATION

Copending application Ser. No. 08/889,793 filed concurrently herewith and assigned to the assignee hereof.

BACKGROUND OF THE INVENTION

1. Technical Field of the Invention

The present invention relates to the formulation of effective amounts of at least one polyholoside into cosmetic/pharmaceutical/dermatological compositions, in particular for topical application, to promote the desquamation of the skin and/or to stimulate epidermal renewal and/or to combat aging of the skin.

This invention also relates to a regimen or treatment for promoting the desquamation of the skin and/or stimulating epidermal renewal and thus combating intrinsic and/or extrinsic aging of the skin.

2. Description of the Prior Art

Desquamation is a natural phenomenon associated with the fact that the epidermis, which constitutes the upper layer of the skin, is in constant regeneration. The epidermis consists of several layers of cells, the deepest of which is the basal layer consisting of undifferentiated cells. These cells differentiate and migrate towards the surface of the epidermis over time, traversing the various layers thereof, until they form, at the surface of the epidermis, the corneocytes which are dead cells which are removed by desquamation. This loss of surface is compensated for by the migration of cells from the basal layer to the surface of the epidermis. This amounts to perpetual renewal of the skin. Forced removal of the horny layer accelerates the renewal and makes it possible to effectively combat aging.

At the same time, these cells continue their differentiation, the final stage of which is the formation of corneocytes. These are dead cells which constitute the final layer of the epidermis, namely, the outermost layer also known as the *stratum corneum*.

Aging of the skin resulting from the effects of intrinsic or extrinsic factors on the skin is reflected by the appearance of wrinkles and fine lines, by yellowing of the skin which develops a parchment-like appearance accompanied by the appearance of pigmentation blemishes, by disorganization of the elastin and collagen fibers, promoting a loss of elasticity, flexibility and firmness, and by the appearance of telangiectasias.

Certain of these signs of aging are more particularly associated with intrinsic or physiological aging, i.e., "normal" aging due to age or chronobiological aging, whereas others are more specific for extrinsic aging, i.e., aging caused by the environment in general; this relates more particularly to photoaging due to exposure to sunlight, to light or to any other radiation.

The invention described below concerns intrinsic or physiological aging, as well as extrinsic aging.

The changes in the skin due to intrinsic aging are the consequence of a genetically programmed senescence involving endogenous factors. This intrinsic aging results, in particular, in a slowing of the renewal of the skin cells, which is reflected essentially by the appearance of clinical impairments, such as reduction in the subcutaneous adipose tissue and the appearance of small wrinkles or fine lines, and by histopathological changes such as an increase in the number and thickness of elastic fibers, a loss of vertical fibers from the membrane of the elastic tissue, and the presence of large irregular fibroblasts in the cells of this elastic tissue.

In contrast, extrinsic aging promotes clinical impairments such as large wrinkles and the formation of a flaccid and tanned skin, and histopathological changes such as excessive accumulation of elastic materials in the epidermis and degeneration of the collagen fibers.

Various active agents for combating aging of the skin are known to this art.

Thus, U.S. Pat. No. 4,603,146 describes the use of retinoic acid and derivatives thereof in cosmetic compositions in order to combat aging of the skin.

Too, many patents and publications (see for example, EP-A-413,528) describe the use of, and many commercial cosmetic compositions contain, α-hydroxy acids such as lactic acid, glycolic acid or citric acid for combating aging of the skin.

Lastly, beta-hydroxy acids and, more especially, salicyclic acid and derivatives thereof are known for their desquamating properties (see WO-A-93/10756 and U.S. Pat. No. 4,767,750).

All of these compounds elicit an action against aging of the skin by promoting desquamation, namely, the removal of the "dead" cells located at the surface of the horny layer of the epidermis. This "desquamating" property is also referred to, often erroneously, as a keratolytic property.

However, the compounds of the prior art elicit side effects which include stinging, tightness, heating (or burning) and redness, which are unpleasant to the user.

Serious need, thus, continues to exist for anti-aging agents which elicit an activity that is at least as effective as that of the compounds of the prior art, but which do not present their drawbacks.

SUMMARY OF THE INVENTION

Accordingly, a major object of the present invention is the provision of novel compositions and regimen utilizing same which promote desquamation of the skin and/or which stimulate epidermal renewal, the applications of which do not cause any stinging, tightness, heating, burning or redness which are unpleasant to the user.

Briefly, it has now unexpectedly been determined that topically applying effective amounts of at least one polyholoside onto the skin promotes the desquamation of the skin and/or stimulates epidermal renewal and, thus, combats cutaneous aging.

DETAILED DESCRIPTION OF BEST MODE AND SPECIFIC/PREFERRED EMBODIMENTS OF THE INVENTION

More particularly according to the present invention, formulated into cosmetic compositions, or into pharmaceutical compositions, in particular into dermatological compositions, are effective amounts of at least one polyholoside, such at least one polyholoside or such compositions promoting desquamation of the skin and/or stimulating epidermal renewal and thus combating intrinsic and/or extrinsic aging of the skin.

This invention also features a regimen for the non-therapeutic treatment of the skin which is intended to promote desquamation of the skin and/or to stimulate epidermal renewal and, thus, to combat intrinsic and/or extrinsic aging of the skin.

The polyholosides according to the invention also present other advantages. This permits formulating compositions for promoting desquamation of the skin which are non-irritant or only slightly irritant and only slightly sticky, and which, moreover, have a soft and pleasant feel.

Another advantage presented by the formulation of such polyholosides is to improve the stabilization of the final composition, when it is in emulsion form, by virtue of the self-emulsifying properties of the polyholoside, in particular when it is a polyholoside which comprises a fucose structural unit.

Too, the formulation of a polyholoside into compositions, in particular cosmetic compositions, permits the production of a gelled composition without further addition of a conventionally employed gelling agent. The gel obtained is smooth, clean and unctuous.

Saccharides, of formula $C_n(H_2O)_n$, are generally divided into two categories: oses (monosaccharides) or simple sugars, and osides (saccharides) or combinations of several molecules.

Among the osides or saccharides, there may be distinguished (1) its holosides which are formed solely of sugars, and (2) the heterosides which comprise one or more oses (monosaccharides) and a non-carbohydrate moiety.

Further, among the polyholosides, there may be distinguished the homogeneous polyholosides which result from the combination of the same ose, and the heterogeneous polyholosides which result either from the combination or association of different oses, or from the combination or association of oses having the same empirical formula but different geometrical or optical configurations (D and L isomers for example), also considered herein as different monosaccharides.

It is this latter category, i.e., the heterogeneous polyholosides, which is the more particularly preferred according to the present invention.

Preferably, according to this invention, a heterogeneous polyholoside is used as an active agent to promote desquamation of the skin and/or to stimulate epidermal renewal and, thus, to combat intrinsic and/or extrinsic aging of the skin.

The heterogeneous polyholosides according to the invention comprise only sugars and result from the combination or association of at least two different oses or monosaccharides.

The polyholosides of this invention advantageously comprise from 2 to 10 oses, these compounds being commonly referred to as oligoholosides, or more than 10 oses, these compounds being commonly referred to as polyholosides.

The oses or monosaccharides comprising the polyholosides according to the invention may be selected from among all possible oses, of natural or synthetic origin, in particular such as:

(a) aldoses, for example:
  (i) the pentoses: ribose, arabinose, xylose or apiose, for example;
  (ii) hexoses: glucose, fucose, mannose or galactose, for example;
(b) the ketoses, such as fructose;
(c) the deoxyoses, such as rhamnose, digitoxose, cymarose or oleandrose;
(d) the ose or monosaccharide derivatives, such as uronic acids, for instance mannuronic acid, guluronic acid, galacturonic acid or glycuronic acid, or the itols such as mannitol or sorbitol.

According to this invention, preferred are heterogeneous polyholosides which may comprise at least two oses or monosaccharides selected from among ribose, arabinose, xylose, apiose, glucose, fucose, mannose, galactose, fructose, digitoxose, cymarose, oleandrose, uronic acids and itols.

The polyholosides according to the invention preferably comprise at least one fucose structural unit.

Even more preferably, the polyholoside comprises fucose, galactose and galacturonic acid structural units, and more particularly a linear chain of α-L-fucose, α-D-galactose and galacturonic acid.

The heterogeneous polyholoside preferably comprises at least one fucose structural unit, which is advantageously present in an amount of 10%–90% by weight, preferably 15%–35% by weight, relative to the weight of the polyholoside dry solids.

Per the present invention, a heterogeneous polyholoside alone, or a mixture of heterogeneous polyholosides, may be used.

The polyholoside according to the invention may be an alginate (polymannuronate and -guluronate) such as a sodium alginate, a propylene glycol alginate, a calcium alginate or a glyceryl alginate.

The polyholoside according to the invention may optionally be linear or branched. It may also be substituted, for example by fatty chains, in particular chains comprising 8 to 30 carbon atoms.

The polyholoside of this invention may be of any origin, natural or synthetic. Particularly, a polyholoside prepared from a microorganism such as, for example, *Klebsiella pneumoniae* is employed. Even more particularly, a polyholoside prepared from the strain *Klebsiella pneumoniae subsp. Pneumoniae*, termed BEC 1000, is employed.

When a polyholoside of natural origin, produced from a microorganism, is used, it is generally associated with proteins. In this event, it may be subjected to a proteolytic treatment.

Any technique permitting proteins to be hydrolyzed may then be used. Enzymatic hydrolysis is the preferred.

The polyholoside is advantageously present in the final composition in an amount of from $10^{-3}\%$ to 25% by weight relative to the weight of the composition and preferably from $10^{-2}\%$ to 15% by weight relative to the weight of the composition.

The polyholoside preferably has a viscosity of 800–1200 mPa.s (Brookfield LV31 viscometer, 12 rev/min, at 30° C.) when it is dissolved in water, at a concentration of about 1% by weight.

Thus, the present invention also features compositions for promoting desquamation of the skin and/or stimulating epidermal renewal and, hence, combating intrinsic and/or extrinsic aging of the skin, comprising at least one polyholoside as described above, other than an alginate.

In the compositions according to the invention, the polyholoside is advantageously present in an amount of from $10^{-3}\%$ to 25% by weight, preferably $10^{-2}\%$ to 15% by weight, relative to the weight thereof.

The polyholosides according to the invention may thus be formulated as active agents to promote desquamation of the skin and/or to stimulate epidermal renewal and, thus, to combat intrinsic and/or extrinsic aging of the skin, in particular into compositions for use on the hair, or into compositions for body and/or facial skin.

The subject compositions include topically applicable, cosmetically/pharmaceutically/dermatologically acceptable vehicles, diluents or carriers therefor and may be provided in the form of an emulsion, in particular an oil-in-water or water-in-oil emulsion, or even in the form of a multiple emulsion. They may also be provided in the form of an optionally gelled aqueous solution, or in the form of a lotion, for example a two-phase lotion, a cream, a milk, an ointment, or even a foam.

The compositions of this invention may comprise an oily phase based on animal, vegetable, mineral, silicone, fluoro and/or synthetic oil.

The oily phase may also comprise fatty alcohols or fatty acids, as well as surfactants.

Particularly exemplary thereof are the hydrocarbon oils, such as liquid paraffin or liquid petroleum jelly; perhydrosqualene; arara oil, sweet almond oil, beauty-leaf oil, palm oil, castor oil, avocado oil, jojoba oil, olive oil or cereal germ oil; alcohols such as oleyl alcohol, linoleyl alcohol or linolenyl alcohol, isostearyl alcohol or octyldodecanol. Also exemplary are the silicone oils, such as optionally phenylated PDMSs, for example phenyltrimethicones.

The oily phase may also comprise a makeup removing oil such as a fatty acid ester, in particular the esters derived from a straight or branched chain alcohol having from 1 to 17 carbon atoms and from a straight or branched chain fatty acid having from 3 to 18 carbon atoms.

Particularly representative such esters include dioctyl adipate, 2-ethylhexyl palmitate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprolate, methyl palmitate, butyl myristate, isobutyl myristate, ethyl palmitate, isohexyl laurate, hexyl laurate and isopropyl isostearate.

The oily phase is advantageously present in an amount of from 5%–95% by weight in the case of an emulsion.

The composition according to the invention may also comprise:

(a) an agent which permits the fatty phase to be placed in suspension, for example a copolymer of $C_{10}$–$C_{30}$ alkyl acrylates and of acrylic or methacrylic acid or an ester thereof (Pemulen TR1, Pemulen TR2, Carbopol 1342 from Goodrich); or an acrylamide/methylpropanesulfonic acid copolymer (Sepigel from Seppic), and/or (b) an agent for dispersing the fatty phase, such as an emulsifying system or a vesicular system based on vesicles, optionally of nanometric size, comprising ionic lipids (liposomes) or nonionic lipids, and in particular the emulsifying systems well known to this art, comprising glyceryl stearate/PEG 100 stearate (CTFA), cetyl alcohol and of stearyl alcohol.

The compositions of the invention too may comprise an agent for modifying its viscosity, in order to obtain relatively gelled textures, such as:

(i) the cellulose derivatives (carboxymethylcellulose, hydroxyethylcellulose, hydroxypropylmethylcellulose);

(ii) the natural gums, such as xanthan gum, guar gum or carob gum, scleroglucans, chitin derivatives, chitosan derivatives and carrageenans;

(iii) the polycarboxyvinyl derivatives of the Carbomer type (marketed by Goodrich under the trademarks Carbopol 940, 951 and 980, or by 3V-SIGMA under the trademarks Synthalen K or Synthalen L).

The compositions according to the invention may also comprise, in known fashion, adjuvants and additives that are commonly used in this art, such as preservatives, antioxidants, fragrances, fillers such as kaolin or starch, or even hollow microspheres, pigments, colorants, UV screening agents, sequestering agents, essential oils, dyestuffs, hydrophilic or lipophilic active agents such as moisturizing agents, in particular glycerol and butylene glycol, anti-inflammatory agents such as allantoin and bisabolol, anti-free-radical agents such as vitamin E or derivatives thereof, calmants or soothing agents such as cornflower water and extract of iris, depigmenting agents, biological active agents such as urea, amino acids, vitamins and derivatives thereof, proteins, salicylic acid and derivatives thereof, α-hydroxy acids, pyrrolidone carboxylic acid and salts thereof, and ceramides.

Of course, one skilled in this art will take care to select this or these optional additional compounds, and/or the amounts thereof, such that the advantageous properties of the compositions according to the invention are not, or are not substantially, adversely affected by the addition envisaged.

The subject compositions preferably have a pH which does not adversely affect the skin, generally ranging from between 5 to 8, preferably a pH of from 5.5 to 7.5.

In order to further illustrate the present invention and the advantages thereof, the following specific examples are given, it being understood that same are intended only as illustrative and in nowise limitative.

EXAMPLE 1

In this example, the capacity of a fucose-rich polyholoside (O.F.) according to the invention to promote desquamation was studied.

This test of in vitro screening of an active agent with regard to desquamation was carried out on differentiated human keratinocytes. The principle of the test was based on the fact that desquamation induces the release of corneocytes. The desquamating power of the test product will be greater, the larger the number of corneocytes released.

The test procedure was as follows: starting with biopsies of human skin, the keratinocytes obtained by separation of the epidermis were dissociated by enzymatic action with trypsin and were cultured at a concentration of $2 \times 10^5$ cells/ml. The growth and differentiation of the keratinocytes was obtained by culturing for 10 to 20 days in a specific medium. Next, after removal of the culture medium, the activity of the test product was evaluated. For this, two samples were taken at T0 and T60, namely, before adding the product and 60 minutes after this addition. The samples thus taken were analyzed with a flow cytometer in order to count the population of corneocytes. The flow cytometer made it possible to distinguish the populations of corneocytes and of keratinocytes by treatment with acridine orange which is specific for cellular DNA. This staining was specific for the keratinocytes since normal corneocytes have no nucleus and thus no DNA.

The cellular detachment index was determined by the difference between T60 and T0. The same measurement was taken for a control containing no test product, since the experiment inevitably produced a release of corneocytes, even in the absence of active agents.

The test was carried out on a polyholoside prepared from the strain *Klebsiella pneumoniae subsp. Pneumoniae* which had been subjected to a proteolytic treatment (O.F.). This polyholoside, having a molecular weight of less than 10,000 Da, was obtained in the laboratory after hydrolysis of a fraction of bacterial polysaccharide.

The results of these studies are reported in the following Table:

TABLE

|      | Reference*<br>$5 \times 10^{-5}$M<br>0.00132% | O.F.<br>0.00132% | O.F.<br>0.000132% | O.F.<br>0.0000132% |
| --- | --- | --- | --- | --- |
| O.F. | 108.7 +/− 4.2 | 207.9 +/− 6.1 | 139.1 +/− 6.7 | 30.5 +/− 3.6 |

*Reference: 2-hydroxy-5-octanoylbenzoic acid, which is known to promote desquamation (see FR-85/06953, assigned to the assignee hereof).

The results are given as a % of activity relative to the control consisting of an identical culture in the absence of compound.

The O.F. activity on the cellular detachment was thus considerable. This dose-dependent activity was higher (as a % equivalent) than that of the reference.

EXAMPLE 2

Examples of formulations illustrating the invention. These compositions were formulated by simply intimately mixing the various components.

| Composition 1 (Face milk): | |
| --- | --- |
| Liquid petroleum jelly | 7.0 g |
| O.F.* | 10.0 g |
| Glyceryl monostearate, polyethylene glycol stearate (100 EO) | 3.0 g |
| Carboxyvinyl polymer | 0.4 g |
| Stearyl alcohol | 0.7 g |
| Soya bean proteins | 3.0 g |
| NaOH | 0.4 g |
| Preservative | qs |
| Water | qs 100 g |

This composition was in the form of a face milk having good cosmetic properties and being soft and comfortable to use.

The pH of the composition was about 5.5.

| Composition 2 (Lotion): | |
| --- | --- |
| O.F.* | 5.0 g |
| 2-ethylhexyl palmitate | 10.0 g |
| Cyclopentadimethylsiloxane | 20.0 g |
| Butylene glycol | 5.0 g |
| Preservative | qs |
| Water | qs 100 g |

This lotion, which contained no surfactant, promoted desquamation of the skin.

| Composition 3 (Milk): | |
| --- | --- |
| Octyl palmitate | 35.0 g |
| Glycerol | 2.0 g |
| O.F.* | 15.0 g |
| Crosslinked polymer of C10–C30 acrylates/alkylacrylates | 0.1 g |
| Triethanolamine | 0.1 g |
| Wheat amino acids | 1.0 g |
| Preservative | qs |
| Water | qs 100 g |

The milk obtained, which contained no surfactant, had good cosmetic properties.

| Composition 4 (Facial gel): | |
| --- | --- |
| Glycerol | 10.0 g |
| O.F.* | 20.0 g |
| Disodium cocoamphodiacetate | 1.0 g |
| Preservative | qs |
| Water | qs 100 g |

The gel obtained has good cosmetic properties.

| Composition 5 (Gel for cleansing with water): | |
| --- | --- |
| Butylene glycol | 7.0 g |
| Sodium lauroyl sarcosinate | 4.0 g |
| O.F.* | 4.0 g |
| Triethanolamine | 0.8 g |
| Carbomer | 0.5 g |
| Preservative | qs |
| Water | qs 100 g |

The gel obtained had good cosmetic properties. O.F.*: polyholoside comprising fucose, galactose and galacturonic acid, prepared from the strain *Klebsiella pneumoniae subsp. Pneumoniae,* which had been subjected to a proteolytic treatment, marketed by Solabia.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for promoting desquamation of the skin of a mammalian organism in need of such treatment and/or to stimulate epidermal renewal and/or inhibit intrinsic and/or extrinsic cutaneous aging, comprising topically applying to the skin of such organism, a cutaneous aging-inhibitory effective amount of the cosmetic/pharmaceutical/dermatological composition suited to promote desquamation of mammalian skin and/or to stimulate epidermal renewal and to inhibit intrinsic and/or extrinsic aging thereof, comprising a cutaneous aging-inhibitory effective amount of at least one polyholoside, in a topically applicable, cosmetically/pharmaceutically/dermatologically acceptable vehicle, carrier or diluent therefor.

2. A method as defined by claim 1 for promoting desquamation of the skin of a mammalian organism in need of such treatment and/or to stimulate epidermal renewal and/or inhibit intrinsic and/or extrinsic cutaneous aging, comprising topically applying to the skin of such organism, a cutaneous aging-inhibitory effective amount of the cosmetic/pharmaceutical/dermatological composition wherein said at least one polyholoside comprises a heterogeneous polyholoside.

3. A method as defined by claim 1 for promoting desquamation of the skin of a mammalian organism in need of such treatment and/or to stimulate epidermal renewal and/or inhibit intrinsic and/or extrinsic cutaneous aging, comprising topically applying to the skin of such organism, a cutaneous aging-inhibitory effective amount of the cosmetic/pharmaceutical/dermatological composition, wherein said at least one polyholoside comprises at least two monosaccharides selected from among the aldoses, ketoses, deoxyoses, derivatives of monosaccharides and mixtures thereof.

4. A method as defined by claim 3 for promoting desquamation of the skin of a mammalian organism in need of such treatment and/or to stimulate epidermal renewal and/or inhibit intrinsic and/or extrinsic cutaneous aging, comprising topically applying to the skin of such organism, a cutaneous aging-inhibitory effective amount of the cosmetic/pharmaceutical/dermatological composition, wherein said at least one polyholoside comprising at least two monosaccharides selected from among ribose, arabinose, xylose, apiose, glucose, fucose, mannose, galactose, fructose, digitoxose, cymarose, oleandrose, uronic acids and itols.

5. A method as defined by claim 1 for promoting desquamation of the skin of a mammalian organism in need of such treatment and/or to stimulate epidermal renewal and/or inhibit intrinsic and/or extrinsic cutaneous aging, comprising topically applying to the skin of such organism, a cutaneous aging-inhibitory effective amount of the cosmetic/pharmaceutical/dermatological composition, wherein said at least one polyholoside comprises at least one fucose structural unit.

6. The method as defined by claim 1, wherein said at least one polyholoside comprises fucose, galactose and galacturonic acid structural units.

7. The method as defined by claim 1, wherein said at least one polyholoside comprises a linear chain of α-L-fucose, α-D-galactose and galacturonic acid.

8. The method as defined by claim 1, wherein said at least one polyholoside comprises an alginate.

9. The method as defined by claim 1, wherein said at least one polyholoside is selected from the group consisting of sodium alginate, propyleneglycol alginate, calcium alginate, and glyceryl alginate.

10. The method as defined by claim 1, wherein said at least one polyholoside comprises at least one fatty hydrocarbyl chain having 8–30 carbon atoms.

11. The method as defined by claim 1, wherein said at least one polyholoside is obtained from a microorganism.

12. The method as defined by claim 1, wherein said at least one polyholoside is obtained from *Klebsiella pneumoniae*.

13. The method as defined by claim 12, wherein said at least one polyholoside is obtained from the strain *Klebsiella pneumoniae subsp. Pneumoniae* (BEC 1000).

14. The method as defined by claim 1, wherein said at least one polyholoside has been proteolytically treated.

15. The method as defined by claim 1, wherein said at least one polyholoside is administered in a composition which comprises from $10^{-3}$% to 25% by weight thereof.

16. The method as defined by claim 15, wherein said administered composition is in a form selected from the group consisting of an emulsion, an aqueous solution which is optionally gelled, a lotion, a two-phase lotion, a cream, a milk, an ointment, and a foam.

17. The method as defined by claim 5, wherein said at least one fucose structural unit in said at least one polyholoside constitutes 10%–90% by weight of said polyholoside.

18. The method as defined by claim 17, wherein said at least one fucose structural unit comprising said at least one polyholoside constitutes from 15%–35% by weight thereof, relative to the weight of the polyholoside.

19. The method as defined by claim 18, wherein said at least one polyholoside is administered in a composition comprising from $10^{-2}$% to 15% by weight of said polyholoside.

\* \* \* \* \*